(12) United States Patent
Jones et al.

(10) Patent No.: US 6,301,371 B1
(45) Date of Patent: *Oct. 9, 2001

(54) OBJECT IDENTIFICATION SYSTEM APPLICATIONS

(76) Inventors: Mark F. Jones, 6310 Rustling Way, San Antonio, TX (US) 78249; James C. Lyman, 238 Circle Dr., Pipe Creek, TX (US) 78063

( * ) Notice: Subject to any disclaimer, the term of this patent is extended or adjusted under 35 U.S.C. 154(b) by 0 days.

This patent is subject to a terminal disclaimer.

(21) Appl. No.: 09/430,792

(22) Filed: Oct. 30, 1999

Related U.S. Application Data

(63) Continuation of application No. 08/946,279, filed on Oct. 7, 1997, now abandoned, which is a continuation-in-part of application No. 08/517,378, filed on Aug. 21, 1995, now Pat. No. 5,764,785.

(51) Int. Cl.⁷ ....................................................... G06K 9/00
(52) U.S. Cl. ............................ 382/106; 382/312; 382/321
(58) Field of Search ..................................... 382/312, 321, 382/106; 356/3.01, 11, 51, 432, 405; 701/50; 313/570, 487

(56) References Cited

U.S. PATENT DOCUMENTS

| | | | |
|---|---|---|---|
| 3,670,193 | * | 6/1972 | Thorington et al. ................. 313/487 |
| 4,853,529 | * | 8/1989 | Meyers ........................... 250/213 VT |
| 4,947,044 | * | 8/1990 | Pinson .................................. 250/330 |
| 4,991,183 | * | 2/1991 | Meyers .................................. 372/100 |
| 5,042,048 | * | 8/1991 | Meyer .................................... 372/108 |
| 5,056,097 | * | 10/1991 | Meyers ................................... 372/38 |
| 5,208,753 | * | 5/1993 | Acuff .............................. 364/424.07 |
| 5,272,518 | * | 12/1993 | Vincent ................................. 356/405 |
| 5,323,085 | * | 6/1994 | Genz ..................................... 313/570 |

* cited by examiner

*Primary Examiner*—Jose L. Couso
*Assistant Examiner*—Anh Hong Do
(74) *Attorney, Agent, or Firm*—John G. Costa (57) ABSTRACT

The invention introduces applications of the use of coherent and non-coherent light in the high wavelengths of the visible spectrum and in the near wavelengths of the infrared spectrum. The applications include a system for the identification of objects under varying light conditions, a system to determine the distance to and size of objects under observation, and a movement sensor system to detect a significant change of position of objects under observation.

20 Claims, 5 Drawing Sheets

OBJECT IDENTIFICATION SYSTEM APPLICATIONS

This is a continuation of U.S. patent application Ser. No. 08/946,279, now abandoned, which was filed on Oct. 7, 1997 as a continuation-in-part of U.S. patent application Ser. No. 08/517,378 filed on Aug. 21, 1995, now U.S. Pat. No. 5,764,785.

FIELD OF THE INVENTION

The present invention relates to object identification under diverse and changing light conditions. Specifically, it relates to a system for the detection and identification of objects, hidden marks, and faults.

BACKGROUND OF THE INVENTION

Night observation systems are well known in the prior art. The roots of these systems can be traced back to before World War II.

Night observation systems are generally divided into active and passive systems. Some night observation systems work by flooding an area under observation with infrared energy.

Active systems have an infrared filter that uses a special lens coating. When infrared light passes through a filter designed to transmit infrared light below 900 nanometers, the filter glows. An auxiliary source of infrared light can be used to illuminate the object under observation. Objects in the observation area reflect infrared energy back to the sensor in the imaging device. Since the glowing filter is visible and reveals the position of the light source, a disadvantage of these active systems is that the location of a covert observer may be revealed. Other active systems use light sources such as infrared lasers which do not require the concomitant use of a filter.

As technology developed some of the disadvantages of active systems were overcome by the use of passive imaging systems. Passive systems usually do not disclose the location of the observer, since they do not emit visible light. Due to their low resolution, the main disadvantage of these systems is the difficulty encountered in distinguishing the object under observation from background noise, such as infrared energy from other sources. Another example of a problem encountered with low resolution is that, in military situations, during combat maneuvers, camels can be confused for tanks.

There are currently at least two types of passive night vision systems.

One type, known as a thermo-imaging system, picks up the emission of heat energy from the objects under observation. A thermo-imaging system detects long wavelength, for example 8–14 micron, infrared radiation emitted from objects as a result of their temperature, usually −20° to +2500° F. A disadvantage of this type of system is that the resultant image lacks clear, identifying qualities. This is particularly disadvantageous in a law enforcement scenario where a police officer must be able to identify the suspect being imaged in order to maintain a proper chain of custody. With thermo-imaging systems, it is difficult not only to maintain a proper chain of custody but also to distinguish friend from foe. Another disadvantage of the thermo-imaging system is that distortion occurs when the system is exposed to visible or infrared light from, for example, a headlight, a flashlight or the sun. A further disadvantage of the thermo-imaging system is that most systems are designed to be used with an eyepiece for viewing. This decreases the peripheral vision and increases the vulnerability of the observer.

A second type of passive night vision system is called a light intensifier system. A light intensifier system takes a very low level of visible light and magnifies it until it is visible to the naked human eye. Unlike the other described systems, the light intensifier system works in the visible spectrum The light intensifier system does not work in a totally dark environment. Another difficulty with the light intensifier system is that the image produced is green, and usually "grainy" or blurred. Furthermore, distortion occurs when the system is exposed to visible or infrared light from, for example, a headlight, a flashlight or the sun. Light intensifier systems are usually constructed in a binocular or scope configuration which decreases the peripheral vision and increases the vulnerability of the observer.

Thus, both thermo-imaging systems and light intensifier systems have relatively low resolution and create a shadowy image, can be damaged when subjected to high intensity light sources, and may decrease the peripheral vision and increase the vulnerability of the observer.

An example of a hybrid system is that of a light intensifier system with laser illumination. This system uses the traditional, passive, light intensification method of imaging supplemented by an infrared laser light illumination of the field of view. The laser has the capability of "viewing" for great distances. However, the image is usually viewed through an eyepiece and appears green and grainy. Also, compared to the non-coherent light sources used in this invention, the laser does not provide as high a reflective factor or as wide an area of illumination.

With all of the conventional systems, it is difficult to obtain an accurate description of the subject or terrain under observation or to determine if the subject being viewed is holding a weapon.

Also, it is believed that none of the conventional systems accurately determine the distance of an object under observation from the point of observation. As a knowledge of the distance to an object is necessary for the determination of the size of that object, the distance to an object is critical for complete object identification. For example, determining the distance to an object and calculating the size of that object can help distinguish whether the object is an adult or a child.

Night observation systems have been disclosed by Meyers in U.S. Pat. Nos. 4,991,183; 4,853,529; 5,042,048; and 5,056,097. Meyers generally discloses an intensification system that uses laser light to supplement the available unseen light. This illuminates an area through the use of infrared lasers which generate coherent light in the observed area. The object under surveillance is displayed as a green image using an eye piece.

Pinson, in U.S. Pat. No. 4,947,044 for a method and apparatus for covertly viewing a target, disclosed the selection of a frequency band of infrared radiation having the least effective transmittance properties of all frequencies of infrared radiation in given atmospheric conditions to illuminate a target and the detection of the reflection of that selected frequency band of infrared radiation from that target. In Pinson, at sea level, all the bands have wavelengths of greater than 1.35 microns.

Other known systems, such as the one designed by Agema Infra Red Systems, use a thermo-imaging system with a video camera format that is used in surveillance applications as well as the thermo measurement of faults in the inspection of electronic or pressurized systems. Thermo-imaging systems have the disadvantage that the quality of the image decreases as the distance of the object under surveillance from the imaging device increases. It is difficult to determine, in a short time, the accurate distance to the object under observation. As the object under observation moves, it is also difficult to follow that object with precise accuracy.

In U.S. Pat. No. 4,264,927 Raymond et.al. disclose an apparatus for scanning and recording information on railroad cars moving at high speed in order to facilitate the identification of the railroad cars. The apparatus employs a television type camera having a pick-up device with high resolution. In Raymond, the inventors note that an advantage of their system is the avoidance of the need for special labels and devices.

In U.S. patent application Ser. No. 08/517,378, Jones and Lyman introduced an imaging system comprising a non-coherent light source, a filter means, a first imaging means, and a first display means. That application also introduced a range finder having a low power diode, a lens system, a second imaging means, a second display means and a precalibrated scale. Furthermore, that application introduced a movement sensor having a display driver circuit board, a scan threshold detector, a microchip, and a microcontroller.

In the present invention, Jones and Lyman introduce improvements and additional applications to the invention disclosed in U.S. patent application Ser. No. 08/517,378.

An advantage of the invention disclosed in U.S. patent application Ser. No. 08/517,378 is that non-coherent light is fanned out onto the entire field of view. Compared to the relatively small area that is viewed using the Meyers system, this is an advantage, since the whole area that is viewed by the electro-optic imaging sensor can be displayed on a display screen. The present invention uses near infrared wave lengths giving a high degree of reflection off the surfaces under observation. This provides a more accurate gray scale image with the advantage that the display reveals much more detail of the object under observation. An example of the high resolution that is accomplished with the present invention is that if the object under observation is a human being, the observer can determine by looking at the display screen if the human under observation wears glasses, or if he is carrying any weapons, or other objects.

Another advantage of the use of near infrared light in the present invention is the detection and identification of hidden images, codes or marks. Inks, paints or other markings, which reflect light exclusively in the high wavelengths of the visible spectrum or in the near wavelengths of the infrared spectrum are difficult or impossible to detect with the naked eye. Such inks, paints or other markings are often referred to as invisible or transparent. Hidden images or marks can be placed on objects such as, for example, clothing or boxes. One purpose of the use of hidden images, codes or marks is to determine whether an article is genuine or counterfeit. Another reason for using hidden images, codes or marks is to add information without visually cluttering the surface. For example, in shipping a package, each handler may place his or her mark and date stamp on the package without visibly overwriting other information on the package. A further application is in providing additional information to markings such as bar codes. For purposes of this application the term "hidden marks" comprises hidden images, codes and marks.

A further advantage of the use of near infrared light in the present invention is the detection of faults on objects such as, for example, airplane wings and ceramic tiles. The highly reflective properties of near infrared light facilitates the detection of such faults. Surface faults are detected directly. The detection of surface abnormalities is helpful in indirectly detecting faults below the surface. When a surface abnormality is detected other methods may be used to confirm if a true fault exists.

The present invention also provides the advantage that the range or distance of the object under observation is determined with great accuracy. Knowledge of the distance from the object to the viewer is then utilized to determine the actual size of the observed object. Thus, with the current invention, the viewer can determine not only if the object under surveillance is a human being, but also if the human being is an adult or a child.

It is an objective of the present invention to observe objects, including animals and humans, at night, or in any light condition, without emitting visible light and simultaneously to create an image with enough detail to clearly identify the characteristics of the objects under observation. A high resolution image generally allows one to differentiate objects and to distinguish, for example, a human from a weight or structure. If the object is human, it may allow one to determine precise characteristics such as sex, attire and objects that the person is carrying It is another objective of the present invention to enable the user to determine the exact distance from the observation point to the object or objects under surveillance and to estimate the size of the object under observation. Therefore, if the object is human, it may allow one to distinguish an adult from a child. It is another objective of the present invention to create a high resolution image so that small scale movement of the observed object can be detected, without confusing it with other environmental factors. It is another objective of the invention to detect when the observed object makes any significant moves and to distinguish mobile objects from stationary objects. It is another objective of the invention to detect and identify hidden, transparent or "invisible" markings or images on objects. It is also an objective of the invention to detect faults in the surfaces of objects. Other objectives of the invention will be apparent from the specification and claims.

Furthermore, the principles disclosed in this invention can be utilized in conjunction with more conventional systems, such as light intensifier systems and systems employing laser light sources, to improve those systems. A further use of the principles disclosed in this invention is in conjunction with camcorders or video cameras.

SUMMARY OF THE INVENTION

This application introduces uses of coherent and non-coherent light in the high wavelengths of the visible spectrum and in the near wavelengths of the infrared spectrum An object identification system comprising an imaging system that uses non-coherent broad band light invisible to the naked eye to generate a high resolution image of the object under observation, a range finder that determines the actual distance to the object under observation and a movement sensor for detecting the movement of the object under observation was introduced by Jones and Lyman in U.S. patent application Ser. No. 08/517,378.

In application Ser. No. 08/517,378, non-coherent light is filtered and projected onto an area to be observed. In the present application it is noted that a light source which selectively emits light in the preferred range obviates the need for filtering said light. In particular, laser illumination of light in the preferred range and light emitting diode (LED) illumination of light in the preferred range are effective light sources. Either a visible light emitting diode or an infrared light emitting diode can be used depending on the application and desired range of light.

The imaging system comprises a light unit, imaging means, and transmission means. The light unit and imaging means do not have to be in the same housing. The imaging means of this invention can be used without the light unit. The light unit projects light in the desired range. The light unit comprises either a light source alone or a light source and one or more filters which filter the light emitted from the light source. Light, both that light projected from the light unit and available ambient light, is reflected from the object under observation to the imaging means. The imaging means comprises a lens and an electro-optic imaging device which is sensitive to available visible light and infrared light. The imaging means may also comprise an optional light intensification means placed between the lens and the electro-optic imaging device. The imaging means may also comprise one or more infrared pass filters. The electro-optic imaging device translates the light received through the lens into a first electronic signal. It is preferred that the light received by the electro-optic imaging device contains infrared light in the near infrared range. Thus, the lens is preferably devoid of a spot filter. The lens is preferably interchangeable, so that the system can employ any lens, including wide angle and telescopic lenses. Also, preferably, any filters employed in either the light unit or the imaging means are interchangeable so that the system can employ a variety of filters dependent on the intended use.

Importantly, the imaging means is used alone, without the light source, for certain applications. An imaging means comprising a lens and an imaging device is commonly used in camcorders and video cameras. The camcorders and video cameras in common use employ lenses which comprise spot filters. In fact, the applicants know of no camcorders or video camera which do not employ lenses which comprise spot filters. As spot filters filter out infrared light the advantages of infrared light are negated by the use of a spot filter. The imaging means introduced in this invention comprises a CCD electro-optic imaging device and a lens devoid of a spot filter. Filters are added to such an imaging means for applications such as the detection of hidden marks or the visualization of surface abnormalities indicative of faults.

The imaging system also comprises means for transmitting said first electronic signal. The first electronic signal is transmitted from the imaging means via transmission means to, for example, a display device which translates the electronic signal into an image of the object under observation. The image of the object under observation is displayed on the screen of the display device. The display device can stand alone or be integrated into the same housing as the imaging system. In the alternative or simultaneously, the first electronic signal can be transmitted to a storage device, such as a conventional video tape or a computer disc, for later viewing. A further alternative is the transmission of the first electronic signal from the imaging means to a transmitting antenna. The signal is then transmitted to a receiving antenna. For example, the signal can be transmitted from the transmitting antenna to a television station antenna, so that the signal can then be broadcast as desired, as, for example, in news broadcasting or teleconferencing. In another embodiment, the signal is transmitted to a receiving antenna on a helmet which is equipped with a miniaturized display unit, such as an eyepiece.

In military applications, for example, an imaging means is mounted like a scope on a rifle. The first electronic signal is then transmitted from the receiving unit to a transmitting antenna in the butt of the rifle and from the transmitting antenna to a receiving antenna on a helmet worn by a soldier carrying the rifle. The signal is then transmitted from the receiving antenna to a display monitor, such as a miniature eyepiece monitor.

By relating the size of the image displayed on the screen to a pre-calibrated scale on said screen the height of the object can be determined. Alternatively, both the dimensions of the object and the precalibrated scale can be digitalized and the comparison can be made electronically. The calibrated scales are digitalized and digital addressing means are used to translate line positions and objects into digital addresses.

The distance to the object in the image is determined by the use of a low power laser diode which generates a laser beam onto a lens system that fans the laser beam out as an inclined plane of light. When the inclined plane of light crosses an object, a line of light is reflected off the object back to an imaging means. The imaging means translates said line of light into a second electronic signal. Preferably the transmission means is also capable of transmitting the second electronic signal in a manner analogous to the transmission of the first electronic signal. In one embodiment, said second electronic signal is translated into a line which is displayed on the screen of a display means. By relating the position of the line displayed on the screen to a pre-calibrated scale on said screen the distance to the object can be determined. The imaging means and display means of the range finder are the same as the imaging means and display means of the imaging system.

Both the position of the line displayed on the screen and the precalibrated scale can be digitalized and the distance to the object can be determined electronically. The range finder comprises, a low power laser diode to generate a laser beam, a lens system that fans said laser beam out as an inclined plane of light, said plane of light being reflected from said object as a line of light, a digital addressing means for the translation of the visible and infrared light in said line of light into a set of digital object addresses, a set of digitalized precalibrated scale addresses, and means to electronically calculate the distance to said object utilizing said set of digital object addresses and said first set of digitalized precalibrated scale addresses. Preferably, the range finder also comprises means to store said set of digital object addresses. Suitable means for storage include conventional hard drives, floppy drives and other storage devices.

Using the same principles described previously, the dimensions of the image received of a target object is electronically compared to the known dimensions of a reference object, the actual dimensions of the target object are electronically calculated and the dimensions of the target object are displayed, stored or transmitted for use by the observer. The system can comprise one or more computer chips programmed to calculate numerical values corresponding to the height of and distance to an object and then to display those values, for example, on the monitor or on an LED display. In like manner, the relationship of the second electronic signal representing the distance to a target object is electronically compared to an electronic signal representing the distance to a reference object, the actual distance to the reference object is electronically calculated and the distance to the target object is displayed, stored or transmitted for use by the observer.

Thus, through previous calibrations, the distance to and height of the object under observation can be determined either by observing the images in the monitor or by means of electronic calculation. Consequently, complete object identification can be achieved.

The system detects significant movement of the objects under observation. This feature improves distinction of mobile objects, such as humans, from immobile objects, such as statues. The system comprises a movement sensor for detecting the movement of the object under observation and an alarm may be activated when significant movements are detected.

The movement sensor comprises a display driver circuit board which outputs video electronic signals whose voltage levels correspond to the screen positions of the lines displayed on a screen by a range finder and a scan threshold detector which, every set time interval, processes said video electronic signals. The time intervals can be set by the operator or pre-programmed into the movement sensor. For each time interval, the scan threshold detector assigns horizontal and vertical digital addresses to each line displayed on a screen by a range finder, and outputs said addresses as digital address signals. A line may represent an object under observation or a known object. The movement sensor also comprises a microchip to read said digital address signals and to transmit a digital map of said digital address signals to RAM for storage. The RAM is conventional computer RAM which, because it stores a digital map of address signals for each time interval, is also referred to as Map RAM. The movement sensor further comprises a micro controller which, every set time interval, compares the map for the most recent time interval with the map for at least one previous time interval. Again, the time intervals can be set by the operator or pre-programmed into the movement sensor. In addition, the movement sensor comprises an alarm which is activated when the map from the most recent time interval differs from the map of at least one previous time interval. The sensitivity of the alarm, that is, the degree of change which must occur to activate the alarm, can be set by the operator or pre-programmed into the movement sensor. Notably, the accuracy of the movement detector is improved when the movement detector is stationary. In the hand held embodiment of the object identification system, the observer may need to hold the system still for a period of time or, in the alternative, to compare, over a period of time, the position of the object under observation with the position of a known stationary object. Relating the position of an object being observed to the positions of at least one, preferably two and most preferably at least three objects with fixed position improves the accuracy of the movement sensor.

DETAILED DESCRIPTION OF THE INVENTION

Figure 1:
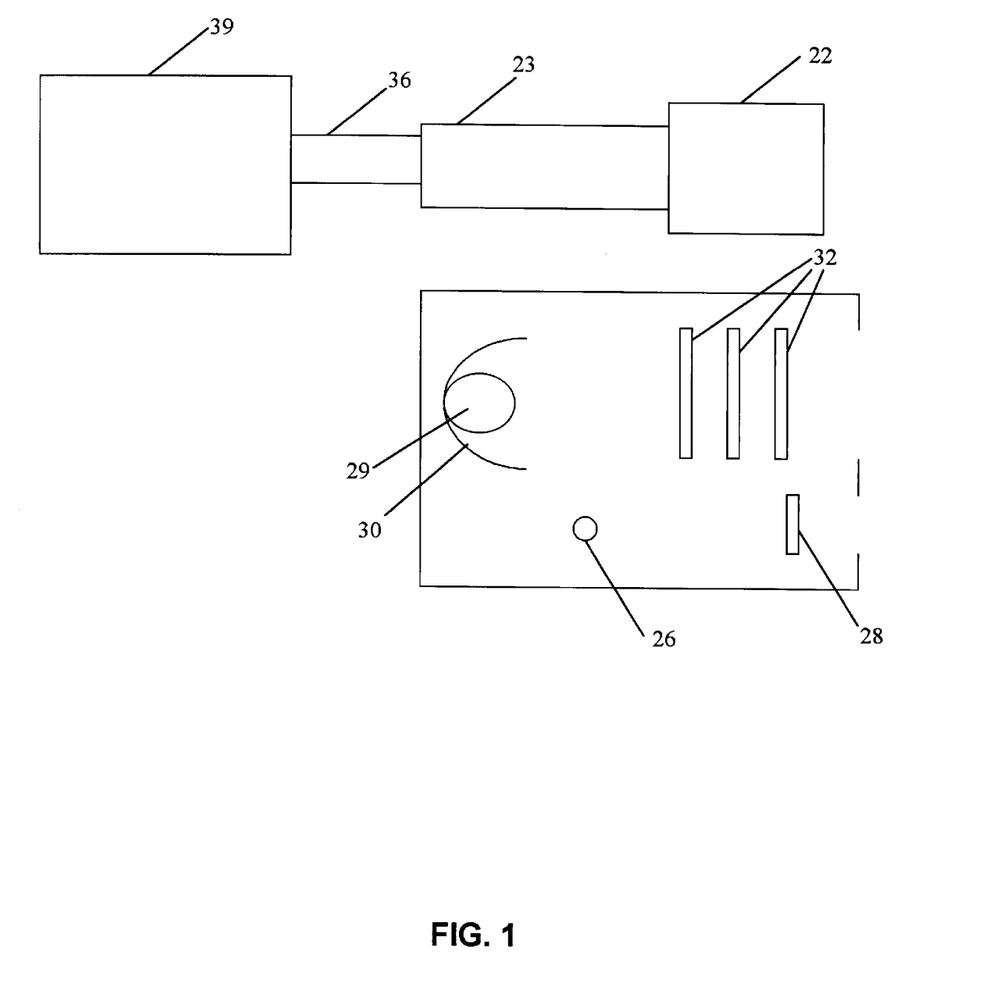
FIG. 1 is a side elevation schematic view showing the components of the invention.

FIG. 1 is a schematic of the invention. The light unit comprises light source 29 and one or more optional light filters 32. The light unit projects light onto the object or objects to be identified. Light source 29 emits light. Light directly emitted from the light source or reflected by reflector 30 then passes through optional filters 32. Filters 32 are infrared pass filters, which allow the passage of infrared light and prohibit the passage of visible light. In the alternative, a clear filter, in place of one or more of the filters can be used. Filters are selected depending on the wave length of light which is desired for illumination of the area under observation. When a clear filter is used, without an infrared filter, the range of the wave lengths of the filtered light will be the same as the range of the wave lengths of the light source. A further alternative is to utilize a light source which emits light which is restricted to a desired range of color temperature and wavelength. In this instance, filters 32 can be eliminated.

Light source 29 is preferably a non-coherent light source with a color temperature between 2000 Kelvins and 6300 Kelvins, and with a color rendition index (CRI) of more than 85. More preferably, the color temperature of the light source is from about 2000 Kelvins to about 5000 Kelvins or has a color rendition index (CRI) of more than about 90. Most preferably the color temperature of the light source is from about 2500 Kelvins to about 3500 Kelvins or has a color rendition index (CRI) of more than about 95. In a preferred embodiment the light source is a halogen or xenon bulb.

When an noncoherent light source is used, it is usually necessary to also use one or more infrared pass filters to achieve the desired wavelength of emitted light from the light unit.

In the alternative, lasers or light emitting diodes (LEDs) which emit light of the desired wavelength can be used without filters.

The light unit preferably projects light in the range of 660 to 1200 nanometers. For night vision applications the range is preferably from 780 to 1000 nanometers, more preferably from 825 to 925 nanometers and most preferably from about 850 nanometers to about 900 nanometers. The highest reflectivity is obtained at about 800 nanometers, but filters glow at that wavelength and can be detected by a person under observation. At 850 nanometers, high reflectivity is still achieved but with less filter glow. In night vision applications such as home camcorder recording in low light conditions or police surveillance from a moving vehicle, the presence of filter glow is unimportant. Whereas, in night vision applications such as hidden security cameras or in military operations, filter glow is undesirable.

For fault detection, the most preferred range is from 780 to 820 nanometers. Surface faults and surface abnormalities indicative of underlying faults appear to be visualized best by the high reflectivity of infrared light near 800 nanometers.

For hidden mark detection, the desired wavelength of light emitted from the light unit is dependent upon the mark being detected. For example, if the hidden mark is drawn with ink which specifically reflects light at 680 nanometers, that is the near infrared range bordering on the visible spectrum, the preferred wavelength of emitted light is about 660 to 700 nanometers, the more preferred wavelength is 670 to 690 nanometers and the most preferred wavelength is about 680 nanometers. It is also possible to detect hidden marks by using a lens filter in the imaging means which permits the passage of light selectively in the desired range. Most preferably, for hidden mark detection, filters permitting the passage of light are used in both the imaging means and the light unit.

The presence of even a small amount of infrared light improves reflectivity. In viewing hidden marks, it is preferable that the imaging means comprise one or more infrared pass filters to enhance the distinction of the hidden mark from the background. The presence of infrared pass filters in the imaging means, light unit, or both, is also at times beneficial in fault detection.

The maximum temperature produced by the light source should be low enough so as not to cause deterioration of the filters or the light housing. Said deterioration is usually not a problem if the heat created by the light source does not exceed 250° F., the housing is insulated and vented, and the light source side of the filters are mirror coated to allow visible light to be reflected back into the housing. The mirror coating of the filter nearest the light source is particularly important to prevent absorption of heat by the filters and thereby to prevent deterioration or cracking of the filters. Likewise, the reflector 30 should be made of aluminum, nickel, silver or plastic and must have a highly reflective, heat resistant coating. Dicroic reflectors should not he used as these reflectors allow infrared light to "escape" through the reflector and thus allow a loss of infrared reflection.

When an object (65 in FIG. 4) is illuminated by the filtered light (71 in FIG. 4) or by available light or an alternative light source, light representing an image of that object is reflected directly or indirectly onto lens 22 of the imaging means. The light representing the image of that object passes through the lens and is received by the electro-optic imaging device 23 of the imaging means and is translated by the electro-optic imaging device into an electronic signal. The imaging means is capable of receiving and translating visible and infrared light. Alternative light sources include non-coherent bulbs, LEDs, or lasers which emit light exclusively in the desired range of wavelengths. The advantage of using a light source which emits light exclusively in the desired range of wavelengths is that the weight of the filter can be eliminated. The advantage of LEDs lies in their small size and low weight, but their low power limits their use to illuminating nearby objects. Laser lighting has the further advantage of providing long distance illumination. However, the area illuminated by a single laser is usually less than a square foot, compared to the 60–100 square foot area illuminated by the non-coherent light used by Jones and Lyman in application Ser. No. 08/517,378 at a distance of 75–100 yards. Pinson suggested projection of a laser beam through dispersion lenses to increase the area of illumination. The applicants suggest that several lasers can be grouped in banks to illuminate areas greater than one square foot, preferably greater than two square feet and more preferably greater than four square feet. For example, a bank of lasers can be placed on a helicopter flying border patrol and one or more imaging means can be aimed to view the area illuminated by the laser banks. Another alternative is to use a reflector behind the laser source to achieve a wider beam. The imaging means can be in the same helicopter, on one or more towers, or on the ground. The electro-optic imaging device 23 is sensitive to low levels of light over a broad range of wave lengths. If an imaging means is equipped with a telephoto lens, an illuminated object can be visualized from a distance. Although, near infrared non-coherent light provides a clearer image than laser light, the imaging means of this invention, when used with laser light, still provides a clearer image than the previously known laser systems. As previously noted, the advantage of laser illumination is that the projected distance of the light energy is greater than that achieved with a non-coherent light source.

When an indirect reflection of the illuminated object is desired, a series of mirrors or lenses may he required to rotate the reflection for viewing. The exact position of those mirrors or lenses would he determined by the relative positioning of lens 22 to the reflected beam.

In a preferred embodiment, the electro-optic imaging device 23 is highly sensitive to the short wavelengths of the infrared spectrum, i.e. the near infrared range, and is sensitive to low levels of available light. However, unlike the previously known light intensification systems, the electro-optic imaging device is not subject to damage when exposed to high intensity light sources such as headlights and the sun. Furthermore, the unique characteristics of the electro-optic imaging device of this invention include the capability of being used for observation in both daylight and total darkness and the capability of switching from daylight to total darkness within seconds and without a change of components. An example of electro-optic imaging devices suitable for use in the preferred embodiment is a miniature solid state CCD image sensor, with sensitivity of at least 1.0 lux, and, most preferably, at least 0.1 lux, and, with capability to support at least 400 (H)×400 (V) pixels, and, preferably, at least, 510 (H)×492 (V) pixels, which can sense light in both the visible and infrared spectrum, and, in particular, can sense reflected light with wavelengths from less than 400 to more than 900 nanometers. Such a CCD sensor can be used in conjunction with a light intensifier or laser with improved image visualization compared to previously designed light intensifier or laser light systems.

The electro-optic imaging device generates electronic signals for the production of images of high resolution and definition. These electronic signals are then transmitted to, for example, a display or a transmitting antenna. As illustrated in FIG. 1, the electronic signal is transmitted through video cable 36 to display 39.

Laser light source 26, which uses a low power laser diode, such as a Class I, 830 nanometer laser with safe sensor, projects a beam of light onto lens 28. Lens 28 disperses the laser beam into a plane of light (60, in FIG. 3). When the plane of light 60 strikes one or more objects, lines, such as 66 and 67 in FIG. 4, will be reflected back to lens 22. Electronic signals representing said lines are then transmitted from electro-optic imaging device 23 through video cable 36.

In a preferred embodiment, laser light source 26 lies at least one inch below light source 29.

Video output electronic signals are transmitted through video cable 36. The video output electronic signals are received and are processed by a display driver circuit board and the image and lines are viewed on the display screen of a standard monitor 39. The monitor can be integrated into the housing or free standing. In the alternative, the video output electronic signals are transmitted for storage to a computer disc, compact disc, or videotape. A further alternative is to transmit the video output electronic signal to a transmitting antenna and from the transmitting antenna to a receiving antenna.

Figure 2:
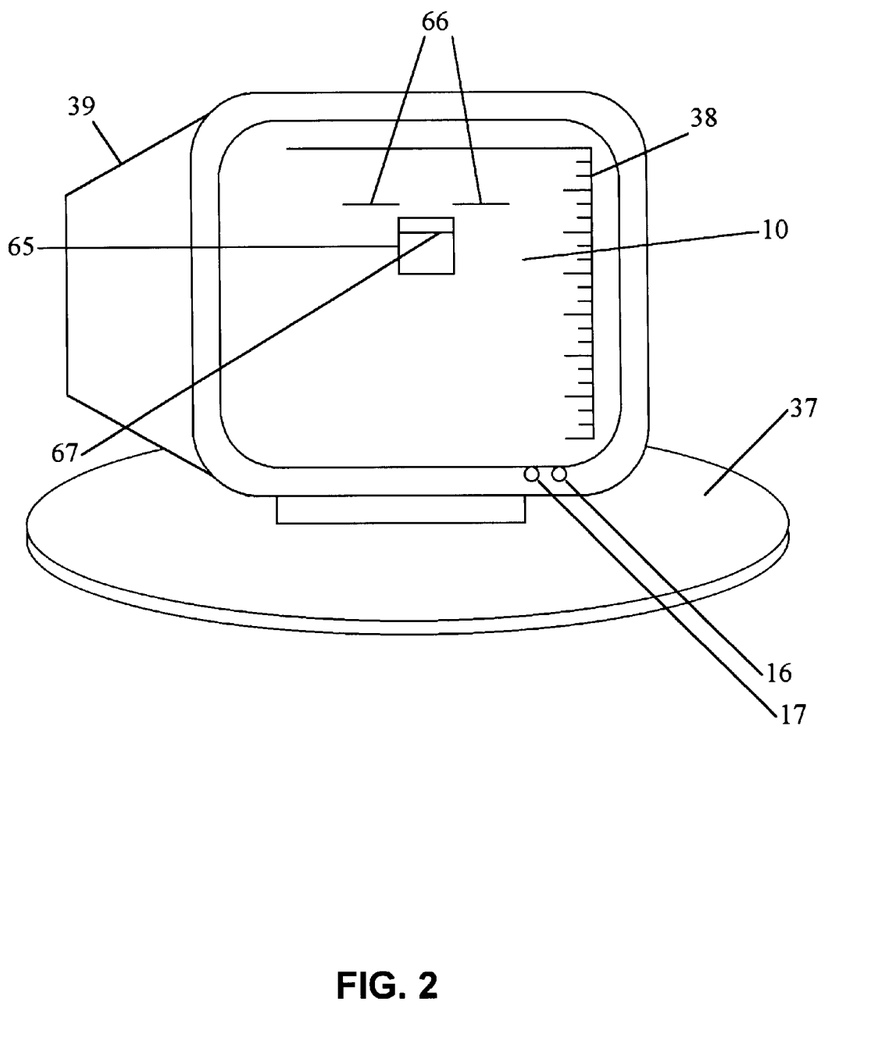
FIG. 2 shows a display monitor of the invention.

The system may be hand held. Preferably, the system comprises a system power switch to turn the system on and off and a light power switch to turn the light source on and off FIG. 2 shows the monitor displaying images from the night illumination system and the range finder. Monitor 39 has base 37. The image of object 65 and the image of the lines 66 and 67 can be adjusted for brightness with brightness control 16 and for contrast with contrast control 17.

Figure 3:
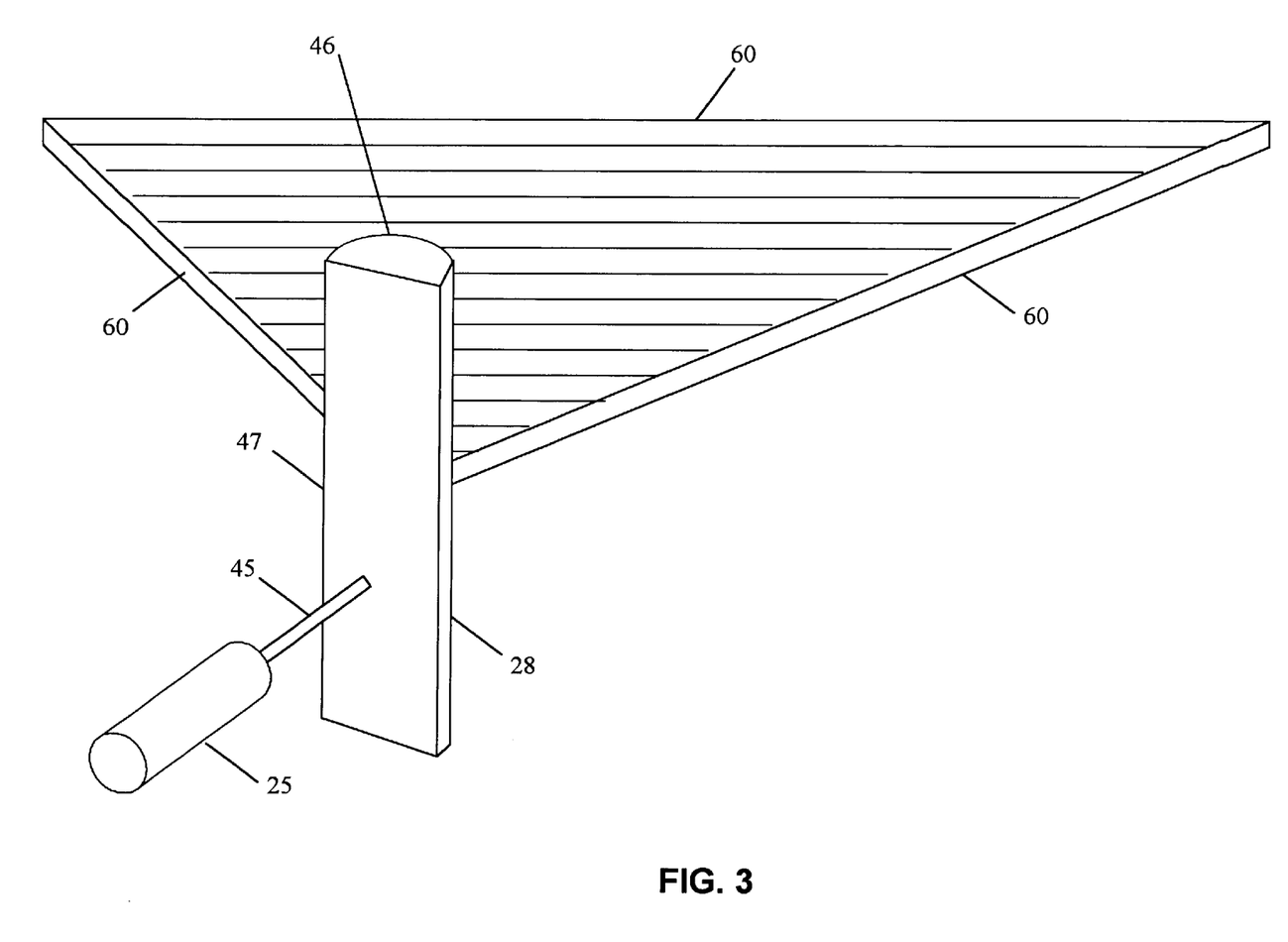
FIG. 3 shows a perspective view of the range finder of the invention.

FIG. 3 illustrates how the laser beam 45 is dispersed. Range finder 25, containing laser light source 26, shown in FIG. 1, emits laser beam 45. The laser beam 45 goes through diversion lens 28. Diversion lens 28 is curved on edge 46 and is straight, not curved, on edge 47. After laser beam 45 goes through diversion lens 28, the plane of light 60 is emitted from diversion lens 28, projecting itself to the area under observation.

Figure 4:
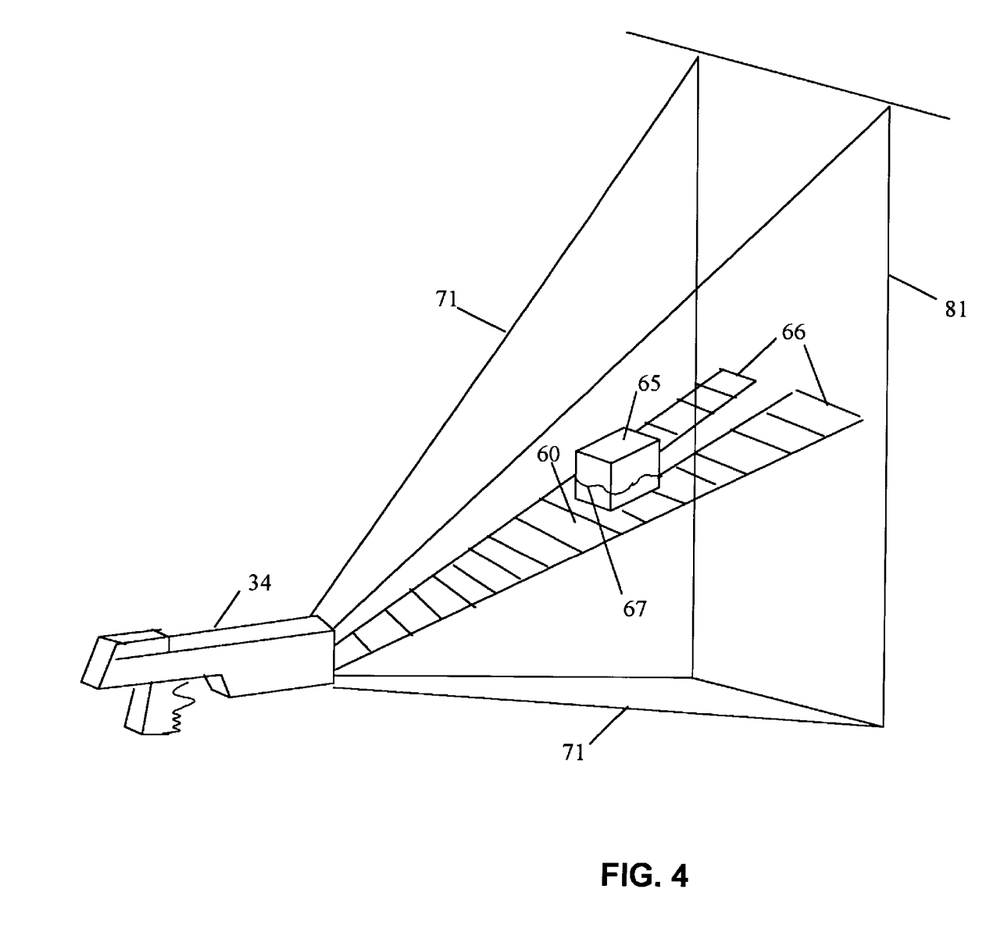
FIG. 4 shows a perspective view of how the range finder and the illumination system work.

FIG. 4 schematically illustrates the use of the range finder in conjunction with the night vision system. FIG. 4 shows an object 65, the plane of light 60, wall 81, filtered light 71 and system controller 34. A range finder is incorporated into system controller 34. The plane of light 60 is projected onto the field of observation. When filtered light 71 is projected towards wall 81 and object 65 is in front of filtered light 71, the area of wall 81 illuminated by filtered light 71 and object 65 reflect back images that are received by the electro-optic imaging device. The projection of the plane of light 60 onto object 65 creates line 67. Line 67 will reflect back to the electro-optic imaging device 23. The parts of the plane of light 60 which do not project onto object 65 will continue to go on until they project onto other objects or dissipate. In FIG. 4, the parts of the plane of light 60 which do not project onto object 65, continue on to project onto wall 81, creating lines 66. Reflections of lines 66 and 67 and object 65 are then received back at lens 22 of the electro-optic imaging device 23. Lines 66, 67 and object 65 are then displayed on a screen 10 of monitor 39 of FIG. 2. By matching lines 66 and 67 to ruler 38, the distance of the object 65 and wall 81 can be determined. Taking the distance to object 65 into account and farther matching the screen height of the image of object 65 to ruler 38, the actual height of object 65 can be determined.

Both the distance and height determinations are done using previously calibrated scales. The higher the position of the line displayed on the screen, the greater is the distance to the object. In other words, the screen contains the tabulated ruler 38. When the user uses the ruler to measure the height of the laser lines 66 and 67 in the display, the tabulated ruler will show the distance to the object. The ruler can also be tabulated to give a value for the screen height of object 65. Using a precalibrated table for screen height and distance, the observer can determine the actual height of object 65. In the alternative, the calibrated scales are digitalized and digital addressing means are used to translate line positions and objects into digital addresses.

Figure 5:
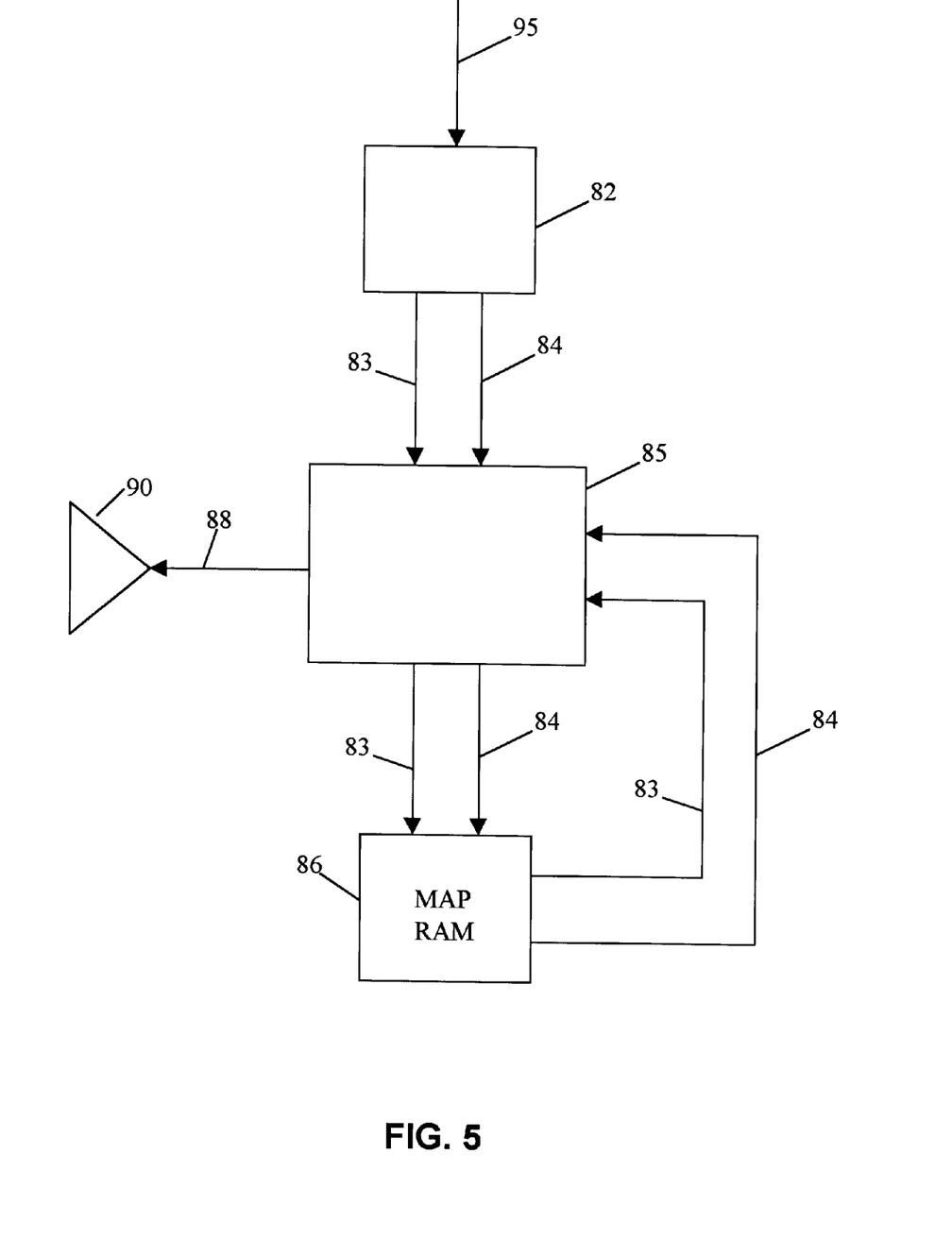
FIG. 5 shows a flowchart of the alarm system.

FIG. 5 is a block schematic diagram of how the motion sensor operates. The motion sensor is incorporated in a display driver circuit board, such as a miniature PC board with standard components. The video output electronic signal 95 comprises voltage levels that are congruent with the screen positions of lines 66 and 67 shown in FIG. 6. The scan threshold detector 82, such as a micro computer, processes the video signal to determine the horizontal and vertical positions of lines 66 and 67 of FIG. 6. After these positions are determined, it outputs a digital address signal 83 of the horizontal position and the digital address signal 84 of the vertical position. These addresses are read by microchip 85, such as a suitable IBM computer chip. Micro-chip 85 will then send digital signal 83 and digital signal 84 to Map RAM 86 where both signals are stored. Standard computer RAM chips can be used for the Map RAM. With address signals 83 and 84 stored in Map RAM 86, the micro controller 85 will continually read the address signals 83 and 84 that are stored in Map RAM 86 and will compare them with the new address signals 83 and 84 that are being sent by threshold detector 82. If an address is different, then movement of an object has occurred, and micro controller 85 emits a signal 88 that activate alarm 90. If the old addresses that are stored at Map RAM 86 are the same as the new addresses that are sent by threshold detector 82 then the path will continue until an address is different.

In the alternative, digital addresses of one or more known fixed objects and one or more observed objects can be mapped at different points of time and the movement sensor can be programmed, using basic geometric and trigonometric relationships, to determine if the object under observation has moved relative to the known fixed objects. For example, the scan threshold detector every set time interval, processes at least one set of digital object addresses, for each time interval, and outputs a set of digital address signals corresponding to said set of digital object addresses.

The image of the precalibrated scale or ruler can also be digitalized and given vertical and horizontal digital addresses. Likewise, the image of an object under observation and, in particular, the boundaries of the image of an object under observation can be digitalized and given vertical and horizontal digital address. Using basic geometric and trigonometric relationships the digital addresses obtained can be used to determine not only the distance to a target object, but also the dimensions of the target object. Numbers representing those distances and dimensions can be electronically and automatically displayed for the user, obviating the need for the user to make a visual and, possible, inaccurate comparison to a precalibrated scale projected on a screen.

Relating the position of an object being observed to the positions of at least one, preferably two, and most preferably three or more objects with fixed positions improves the accuracy of the movement sensor. For example, a patrol car can record a map of an area with known fixed objects and an unknown object on a first pass, or drive by, and compare that first pass map with a second pass map to determine if the position of the unknown object relative to the known fixed objects has changed. As another example, if three known fixed objects and one object under observation are mapped from any point of observation and those same objects are mapped from a second point of observation at a subsequent point in time, one can determine, using basic geometric and trigonometric relationships, if any object under observation has moved relative to any known fixed objects.

Notably, a digital address signal for distance information, determined, for example, by a range finder, for each line can be indexed to the horizontal and vertical digital addresses and added to the map information. Such distance information can be input manually or automatically. In this event, the distance digital address will be processed in the same manner, through the same pathways, as the horizontal and vertical digital addresses.

Digital addressing is done by means of conventional hardware and software.

Importantly, the imaging means is used alone, without the light source, for certain applications. An imaging means comprising a lens and an imaging device is commonly used in camcorders and video cameras. The camcorders and video cameras in common use employ lenses which comprise spot filters. In fact, the applicants know of no camcorders or video camera which do not employ lenses which comprise spot filters. As spot filters filter out infrared light the advantages of infrared light are negated by the use of a spot filter. The imaging means introduced in this invention comprises a CCD electro-optic imaging device and a lens devoid of a spot filter. Filters are added to such an imaging means for applications such as the detection of hidden marks or the visualization of surface abnormalities indicative of faults. Furthermore, a light intensifier can be added for military applications.

The preferred imaging means of this invention comprises a solid state CCD image sensor with at least 1.0 lux sensitivity and preferably at least 0.1 sensitivity and with the capability to support at least 400 (H)×400 (V) pixels, and preferably at least 510 (H)×(492 (V) pixels and a lens devoid of a spot filter with an aperture of at least F 4.0 and preferably at least F 1.4. Said imaging means is capable of translating visible and infrared light, in the range of from less than about 400 nanometers to about 1200 nanometers, reflected from an object into an electronic signal.

The applicants note that the word "object" in "object identification system" is used broadly. For example, people, furniture, houses and vegetation in a camcorder recording are all objects. Also, marks made with "invisible" inks and faults in ceramic tiles are objects.

The foregoing are the preferred embodiments of the invention. However, various changes can be made in the system without departing from the scope of the invention, so the preferred embodiment should not he interpreted as limiting the scope of the invention.

What is claimed:

1. An imaging system comprising:
   a non coherent light source for generating light, said non-coherent light source having a color temperature between 2000 Kelvins and 3500 Kelvins and a color rendition index (CRI) of more than 90,
   a filter means for filtering said generated light, wherein said filter means permits the passage of light in the range of from 800 nanometers to 950 nanometers, an imaging means for the translation of visible and infrared light reflected from an object into an electronic signal, said electronic signal is a video signal for the production of images of said object.

2. The system of claim 1 further comprising transmission means for transmitting said electronic signal.

3. An imaging system comprising a light unit and imaging means, said light unit projects light in the range of from 780 nanometers to 1000 nanometers onto an object, said imaging means comprises a lens and an imaging device, said lens receives light reflected from said object and transmits said reflected light to said imaging device, said reflected light comprises infrared light, said imaging device receives said reflected light and translates said reflected light into an electronic signal, said electronic signal is a video signal for the production of images of said object.

4. The system of claim 3 further comprising transmission means for the transmission of said electronic signal.

5. The system of claim 3 wherein said infrared light is near infrared light.

6. The system of claim 3 wherein said imaging means further comprises at least one filter.

7. The system of claim 6 wherein the object is a fault and the reflected light received by said imaging device comprises light in the range of from 780 nanometers to 820 nanometers.

8. The system of claim 6 wherein the wavelength of light reflected from a target object is known and the light reflected from said target and received by said imaging means is selectively filtered to permit the passage of light in a desired range, said desired range being dependant on the known wavelength of light transmitted from said target.

9. The system of claim 3 wherein said light unit further comprises at least one filter.

10. The system of claim 9 wherein the wavelength of light reflected from a target object is known and the light projected onto said target by said light unit is selectively filtered to permit the passage of light in a desired range, said desired range being dependant on the known wavelength of light transmitted from said target.

11. The system of claim 10 further comprising a light source that emits light in said desired range.

12. The system of claim 3 wherein said imaging device has a sensitivity of at least 1.0 lux.

13. The system of claim 3 wherein said imaging device is capable of supporting at least 400 (H)×400 (V) pixels.

14. The system of claim 3 wherein said lens has an aperture of at least F4.0.

15. The system of claim 3 wherein said imaging device has a sensitivity of at least 0.1 lux.

16. The system of claim 3 wherein said imaging device is capable of supporting at least 510 (H)×492 (V) pixels.

17. The system of claim 3 wherein said lens has an aperture of at least F1.4.

18. The system of claim 3 wherein said imaging device is a solid state CCD image sensor.

19. The system of claim 3 further comprising a conventional system.

20. The system of claim 19 wherein said conventional system is a light intensifier.

* * * * *